United States Patent [19]

Chiang et al.

[11] Patent Number: 4,886,881

[45] Date of Patent: Dec. 12, 1989

[54] PREPARATION OF 2-AMINO TRIAZINES

[75] Inventors: George C. Chiang, Wilmington, Del.; Masuo Toji, Sewell, N.J.

[73] Assignee: E. I. Du Pont de Nemours and Company, Wilmington, Del.

[21] Appl. No.: 351,102

[22] Filed: May 12, 1989

[51] Int. Cl.$^4$ .................. C07D 251/16; C07D 251/42
[52] U.S. Cl. ...................................................... 544/194
[58] Field of Search ......................................... 544/194

[56] References Cited

U.S. PATENT DOCUMENTS 2,206,005  6/1940  Grim .................................. 544/194

Primary Examiner—John M. Ford

[57] ABSTRACT

Process for preparing aminotriazines wherein it is not necessary to make any separations before completing the preparation. The process of the invention involves reacting dicyandiamides with trimethylorthoacetate in the presence of a catalyst to form aminotriazines.

15 Claims, No Drawings

PREPARATION OF 2-AMINO TRIAZINES

BACKGROUND OF THE INVENTION

This invention is directed to a process for preparing aminotriazines wherein it is not necessary to make any separations before completing the preparation. The process of the invention involves reacting dicyandiamides with trimethylorthoacetate in the presence of a catalyst to form aminotriazines.

U.S. Pat. Nos. 4,169,719 and 4,394,506 disclose the preparation of 2-aminotriazines.

DD 252374 discloses the use of cyanoguanidine in the presence of Cu(AC)$_2$ for the preparation of 2-aminotriazine.

*Journal of Organic Chemistry,* 28, 1816 (1963) discloses the preparation of 2-aminotriazines from N-cyanoimino esters and methylisourea.

*Helv. Chim. Acta.,* 33, 1365 (1950) also discloses the preparation of 2-aminotriazines via cyanuric chloride and a Grignard reagent.

SUMMARY OF THE INVENTION

This invention pertains to a novel process for the one-step preparation of 2-aminotriazines of Formula I. One embodiment (Embodiment 1) of the invention consists of reacting dicyandiamide (cyanoguanidine) II with trimethylorthoacetate in the presence of a suitable Lewis acid catalyst such as ZnCl$_2$. In the process of the invention, the postulated intermediates III and IV indicated below are not isolated, but are converted directly to the final triazine product.

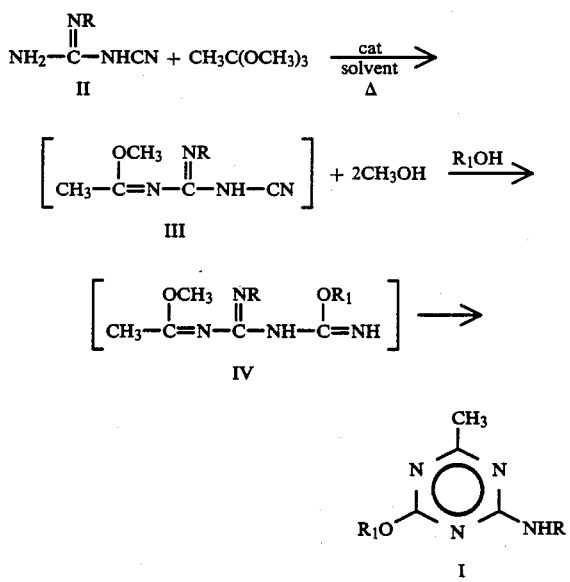

Scheme I wherein
R is H or CH$_3$; and
R$_1$ is C$_1$–C$_3$ alkyl.

Alternatively, a second embodiment (Embodiment 2) of this invention is to generate the trimethylorthoacetate in situ using acetonitrile as the solvent. This is outlined in Scheme II.

Scheme II

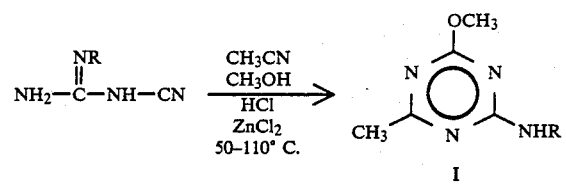

The reaction conditions for Embodiments 1 or 2 are as follows:

| | |
|---|---|
| Solvents | Dimethylformamide, Dioxane, Methylisobutyl ketone, ethers such as diglyme, Dimethyl sufoxide and acetonitrile. |
| Preferred solvents | Dimethylformamide, acetonitrile. |

Thus the invention is a process for the preparation of aminotriazines of the formula

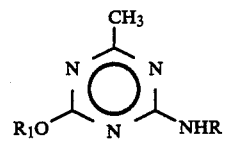

wherein
R is H or CH$_3$; and
R$_1$ is C$_1$–C$_3$ alkyl;
said process comprising reacting dicyandiamide of the formula

where R is as defined above with an amount of 0.5 to 5.0 mol of trimethylorthoacetate per mole of dicyandiamide in the presence of 10 to 50 mol percent of a suitable Lewis acid catalyst and a solvent at 50° to 100° C. and a pressure of 1 to 5 atmospheres for a time of 6 to 48 hours.

The invention also is directed to a process for the preparation of aminotriazines of Formula I above wherein the aforesaid process is conducted in the absence of trimethylorthoacetate and the solvent is acetonitrile.

The instant invention is directed to a new and useful process for the preparation of 2-aminotriazines. This novel process affords good yields of triazines starting with simple and inexpensive reagents. The products of the process, 2-aminotriazines are useful intermediates for the manufacture of herbicides such as sulfonylureas.

DETAILED DESCRIPTIONS OF THE INVENTION

The process of Embodiment 1 of the invention may be carried out by heating a solution of cyanoguanidine, 0.1 to 0.5 mole equivalents of zinc chloride and 0.5 to 2.5 mole equivalents of trimethylorthoacetate together at the reflux point of the solution for approximately 16 hours. More than 2.5 mole equivalents of trimethylorthoacetate may be used. However, the use of 0.5 to 2.5 moles trimethylorthoacetate is the most economical. After cooling, water is added and the resulting solids are collected and dryed. Alternatively, the above procedure may be carried out in the presence of a solvent such as dimethylformamide or acetonitrile.

The process of Embodiment 2 of the invention may be carried out by bubbling excess HCl into a mixture of excess $CH_3CN$ in 1 to 1.1 mole equivalents of methanol. After methanolysis with additional methanol, removal of solids and the majority of solvent via distillation is then followed by the addition of cyanoguanidine and 0.1 to 0.5 mole equivalents of zinc chloride. Following the procedures of Embodiment 1 then results in good yields of the 2-aminotriazine.

The following Examples help further illustrate the invention.

EXAMPLE 1

A mixture of 21.0 g (0.25 mole) cyanoguanidine, 5.0 g zinc chloride and 100 g (0.83 mole) trimethylorthoacetate was heated at reflux (75°–85° C.) for 16 hours. Water (100 ml) was added and the solids were collected on a filter and washed with water. The solids were dried to yield 24.1 g (m.p. 250°–253° C.). This material was assayed by HPLC and determined to be 89% 2-amino-4-methoxy-6-methyltriazine. The yield is 63% of theory.

EXAMPLE 2

A mixture of 21.0 g (0.25 mole) cyanoguanidine, 10.0 g zinc chloride, 60 g of trimethylorthoacetate, and 25 ml of DMF was heated at 80°–85° C. for 16 hours. Water (50 ml) was added and the mixture was filtered, washed with water, and dried to yield 20.2 g of product (m.p. 254°–259° C.). An HPLC assay showed this material to be 99% Compound I, (R=H, $R_1$=$OCH_3$).

EXAMPLE 3

A mixture of 21.0 g (0.25 mole) cyanoguanidine, 10.0 g zinc chloride, 75 g (0.625 mole) trimethylorthoacetate and 50 ml acetonitrile was heated at reflux for 20 hours. Water (50 ml) was added, the reaction was cooled and then filtered. After washing with water and drying, 22.6 g of solids (m.p. 258°–263° C.) were obtained. The product was assayed by HPLC and found to be 99% Compound I, (R=H, $R_1$=$OCH_3$).

EXAMPLE 4

Example 3 was repeated using 10.0 g cupric chloride in place of the zinc chlordie. The material obtained (15.0 g) did not melt below 290° C. The IR spectrum (Nujol mull) displayed a strong band at 2200 $cm^{-1}$ and was different from that of Compound I, isolated previously in Examples 1–3.

EXAMPLE 5

Example 1 was repeated using 5.0 g cupric acetate monohydrate in place of the zinc chloride. Upon filtration, no solids remained on the filter. Compound I, R=H was not formed.

EXAMPLE 6

To a mixture of 300 ml of acetonitrile and 81 ml of methanol, 68.1 g (1.87 moles) of hydrogen chloride was added at 10°–15° C. The reaction mixture was held at 23° C. for 12 hours. Methanol (307 ml, 7.46 moles) was added and the reaction mass was agitated at 20°–25° C. for 12 hours. The reaction mass was filtered and the filtrate was distilled until the pot temperature was 82° C. To the distillation residue, 42.0 g of cyanoguanidine and 20 g of zinc chloride were added. The reaction mass was heated at reflux 71°–81° C. for 16 hours. Water (50 ml) was added and the solids were collected on a filter. After washing with water and drying, 44.0 g of solids (m.p. 259°–263° C.) was obtained. HPLC analysis of the product shows it to be 98.3% Compound I, (R=H, $R_1$=$OCH_3$).

What is claimed is:

1. A process for the preparation of aminotriazines of the formula

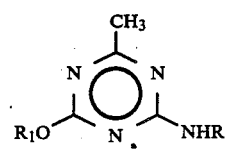

wherein
R is H or $CH_3$; and
$R_1$ is $C_1$–$C_3$ alkyl;
said process comprising reacting dicyandiamide of the formula

where R is as defined above with an amount of 0.5 to 5.0 mol of trimethylorthoacetate per mole of dicyandiamide in the presence of 10 to 50 mol percent of a suitable Lewis acid catalyst and a solvent at 50° to 100° C. and a pressure of 1 to 5 atmospheres for a time of 6 to 48 hours.

2. The process of claim 1 wherein the suitable Lewis acid catalyst is $ZnCl_2$.

3. The process of claim 2 wherein the temperature is 75° to 85° C.

4. The process of claim 2 wherein the pressure is 1 atmosphere.

5. The process of claim 2 wherein the time is 12 to 16 hours.

6. The process of claim 2 wherein 15 to 30 mole percent are used.

7. The process of claim 2 wherein the temperature is 75° to 85° C., the pressure is 1 atmosphere, the time is 12 to 16 hours and the mole percent of catalyst is 15 to 30.

8. The process of claim 1 wherein the trimethylorthoacetate is generated in situ from excess acetonitrile, hydrogen chloride, and methanol.

9. The process of claim 8 wherein the suitable Lewis acid catalyst is $ZnCl_2$.

10. The process of claim 8 wherein the temperature is 75° to 85° C.

11. The process of claim 8 wherein the pressure is 1 atmosphere.

12. The process of claim 8 wherein the time is 12 to 16 hours.

13. The process of claim 8 wherein 15 to 30 mole percent are used.

14. The process of claim 8 wherein the temperature is 75° to 85° C., the pressure is 1 atmosphere, the time is 12 to 16 hours and the mole percent of catalyst is 15 to 30.

15. A process of claim 8 wherein the solvent is excess acetonitrile.

* * * * *